United States Patent [19]
Takahashi et al.

[11] Patent Number: 4,749,657
[45] Date of Patent: Jun. 7, 1988

[54] ORGANIC SPILL MONITOR

[75] Inventors: Yoshihiro Takahashi; Larry E. Maley, both of San Jose, Calif.

[73] Assignee: Xertex Corporation, Santa Clara, Calif.

[21] Appl. No.: 53,527

[22] Filed: May 21, 1987

Related U.S. Application Data

[63] Continuation of Ser. No. 657,503, Oct. 3, 1984, abandoned.

[51] Int. Cl.⁴ .................. G01N 33/18; G01N 31/12
[52] U.S. Cl. ........................ 436/146; 422/68;
422/81; 436/52; 436/150; 436/905
[58] Field of Search ............ 204/158 HE, 162 HE;
250/432 R, 435, 436; 422/68, 81; 436/52, 62,
146, 175-178, 150, 905

[56] References Cited

U.S. PATENT DOCUMENTS

| | | | |
|---|---|---|---|
| 1,969,655 | 8/1934 | Mailey | 250/436 X |
| 2,636,991 | 4/1953 | Postell | 250/436 |
| 3,322,504 | 5/1967 | Capuano | 436/150 X |
| 3,540,849 | 11/1970 | Neti et al. | 436/905 X |
| 4,277,438 | 7/1981 | Ejzak | 250/436 X |
| 4,344,696 | 1/1981 | Wolfel | 436/62 |

FOREIGN PATENT DOCUMENTS 45-15677 6/1970 Japan .................. 436/62

OTHER PUBLICATIONS

Poirier et al.; A New Approach to the Measurement of Organic Carbon; American Laboratory, Dec. 1978, (reprint).

Anatel; The First Practical On-Line Total Organic Carbon Monitor for High-Purity Water, (product publication), 1984.

Primary Examiner—Barry S. Richman
Assistant Examiner—Michael S. Gzybowski
Attorney, Agent, or Firm—Flehr, Hohbach, Test, Albritton & Herbert

[57] ABSTRACT

A sample aqueous stream including one or more organic compounds capable of partial oxidation to acid form are flowed continuously through an ultraviolet light reactor in which the sample is exposed to ultraviolet light in the presence of oxygen under conditions to partially oxidize the organic compounds to convert at least a portion of them to their corresponding ionized organic acids. Thereafter, the sample stream continuously flows through a conductivity cell in which the changing conductivity of the sample is detected as an indication of the presence of organic compounds in the sample stream.

4 Claims, 1 Drawing Sheet

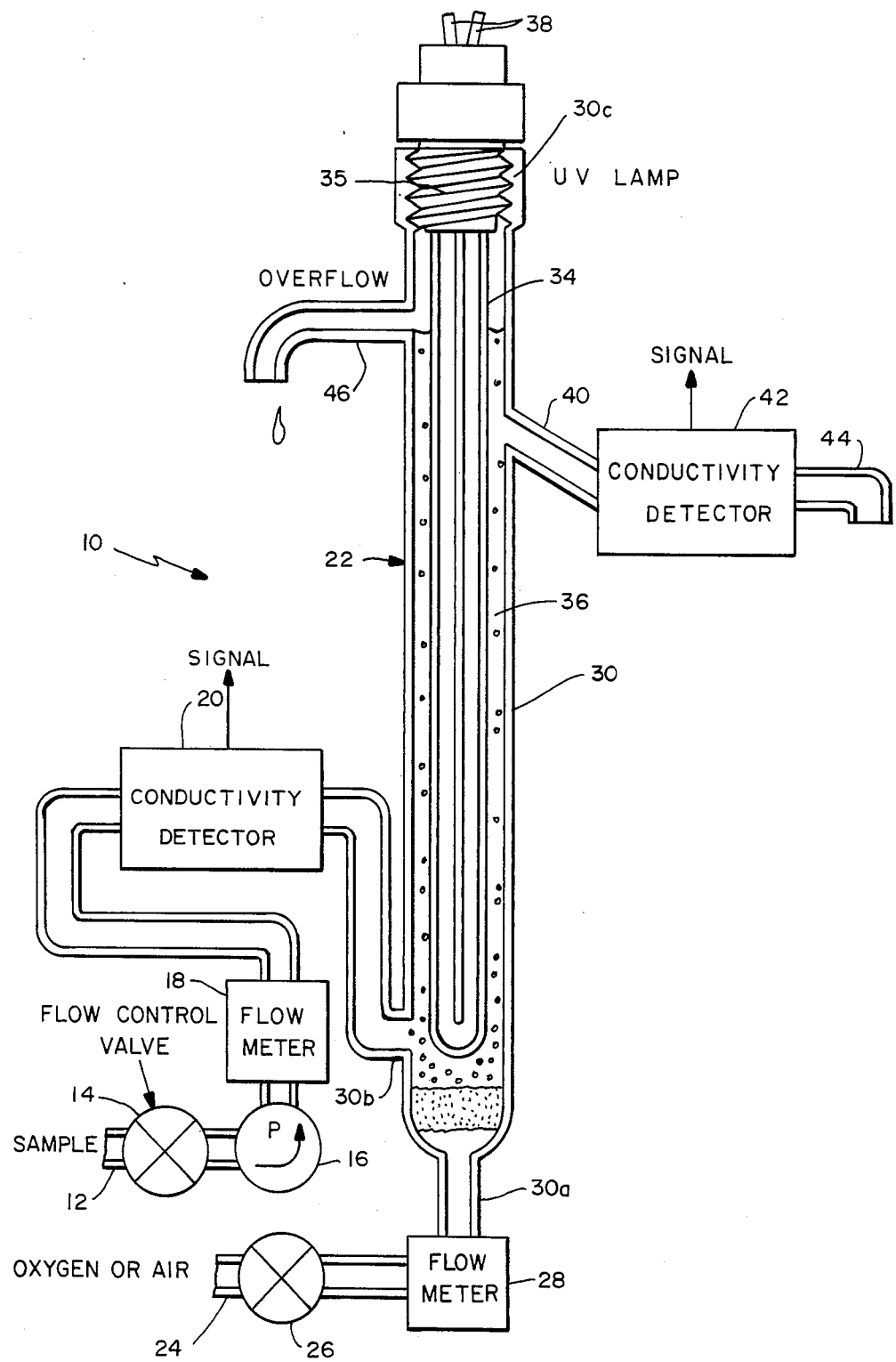

ORGANIC SPILL MONITOR

This is a continuation of application Ser. No. 657,503 filed Oct. 3, 1984, now abandoned.

BACKGROUND OF THE INVENTION

A number of devices monitor the presence of organic compounds in aqueous streams. Potential uses for such devices include the monitoring of aqueous streams in chemical plants, water purification plants, power plants, food processing plants, semiconductor plants, pharmaceutical plants and the like.

In one approach, disclosed in Regan, U.S. Pat. No. 3,958,941, an aqueous sample is periodically injected into a line which feeds into a reactor in which it is exposed to ultraviolet irradiation which oxidizes the organic carbon content to $CO_2$ gas. The generated $CO_2$ is mixed with water in a resistivity (or conductivity) cell which is stated to measure the amount of initially present organic carbon as a decrease in resistance in water present in the resistivity cell. Air strips off water insoluble gases and bubbles through deionized water held separately in the resistivity cell. The gases are reabsorbed therein, and the conductivity is measured as an indication of gases is ionized in the water. Possible gases include $CO_2$ and $H_2S$. This system is primarily useful for analysis of high purity water and is based on the complete oxidation of organics to carbon dioxide. It is a complicated and expensive system to build and its batch-type sample addition limits the time when samples may be detected and requires the presence of a technician to periodically inject sample. Also, it requires complete oxidation to $CO_2$ which is difficult and time consuming.

Another batch-type ultraviolet system is sold by Anatel Instrument Corporation of Boulder, Colo., under the designation A-100 TOC. It suffers from the deficiencies of batch operation discussed above. Also, it is subject to malfunction due to valve opening and closing operations for each cycle. Furthermore, it is relatively expensive because it requires sophisticated electronics to measure rate changes during the oxidation cycle.

SUMMARY OF THE INVENTION

In accordance with the present invention, a sample aqueous stream including one or more organic compounds capable of partial oxidation to acid form are flowed continuously through an ultraviolet light reactor in which the sample is exposed to ultraviolet light in the presence of oxygen under conditions to partially oxidize the organic compounds to convert at least a portion of them to their corresponding ionized organic acid. Thereafter, the sample stream continuously flows through a conductivity cell in which the changing conductivity of the sample is detected as an indication of the presence of organic compound in the sample stream which has been converted to ionized form. Since the partially oxidized organic acids are detected in water, it may be desirable to sparge gases from the liquid stream prior to detection by the conductivity detector in order to remove interference from gases ionized in the liquid such as carbon dioxide. The background conductivity of the entering sample stream may be measured to determine the difference in conductivity caused by ultraviolet exposure. This system is particularly effective for measuring organic compounds in the sample which flow in a relatively constant concentration so that the spill of a chemical into such a constant background sample stream is readily detected.

The ultraviolet reactor includes an ultraviolet lamp with a surrounding flow-through channel through which the sample stream and oxygen continuously pass for exposure of the sample to the ultraviolet light. A conduit connects the liquid outlet from the ultraviolet reactor to a conductivity cell in which the conductivity is measured as an indication of the presence of organic compounds in the sample stream. A second conductivity detector may be included to measure background conductivity prior to passing through the ultraviolet reactor. This continuous monitoring device is a major simplification of devices of the prior art and permits continuous monitoring of a sample stream without periodic sampling. Also, it provides very high sensitivity.

BRIEF DESCRIPTION OF THE DRAWINGS

The sole FIGURE is a schematic representation of a device suitable for performing the present invention.

DETAILED DESCRIPTION OF THE PREFERRED EMBODIMENT

Referring to the FIGURE, a schematic view is illustrated of monitoring apparatus 10 suitable for use in the present system. A sample is continuously withdrawn from the process stream to be monitored. The system is applicable to monitoring flow lines of chemical plants for organic loading and product loss, monitoring water purification streams for raw unfinished water quality, monitoring boiler feed and condensate purity in power plants, monitoring the purity of process water and deionized water in semiconductor plants, food process plants, and the like.

In the illustrated embodiment, a sample from one of the foregoing sources is passed through line 12 into flow control valve 14 and is pumped by pump 16 through flow meter 18, through conductivity detector 20 and into the bottom of vertically disposed ultraviolet reactor 22. The pump is not required when the sample is supplied under adequate pressure. The purpose of optional conductivity detector 20 is to measure the background conductivity of the sample stream prior to treatment in reactor 22 as set out below. Conductivity detector 20 is not necessary where the background conductivity is relatively constant or at a sufficiently low level in comparison to that of the treated product stream. The conductivity detector may be of a conventional type.

A source of oxygen under pressure, such as pure oxygen or air, is directed through line 24, flow control valve 26, flow meter 28, and into the bottom of ultraviolet reactor 22.

Referring specifically to the ultraviolet reactor, it includes an elongate cylindrical housing 30, suitably formed of glass, which narrows to form an inlet neck portion 30a for the oxygen-containing gas and includes a side arm inlet 30b to flow sample into the lower portion of housing 30.

Means is provided for irradiating the liquid stream sample flowing through reactor 22. In the illustrated embodiment, such means includes a conventional ultraviolet lamp 34, typically rated at 30 watts, which is mounted to extend into and concentrically along housing 22 spaced therefrom to form an annular flow-through channel 36 for the continuous passage of sample and gas upwardly through reactor 22 and past the ultraviolet lamp. As illustrated, the lower or upstream side of lamp 34 is disposed generally adjacent to the inlet flow of sample and oxygen gas. Lamp 34 suitably includes a screw-threaded mounting plug 35 which mates with corresponding threads of top opening 30c of housing 30 in a gas-tight fit. Appropriate electrical connections 38 are provided for the ultraviolet lamp.

A liquid outlet conduit or line 40 communicates with an opening in housing 30 to provide an outlet flow path for liquid which has been irradiated in housing 30. Such liquid flows directly through line 40, through conductivity detector 42, and exits via outlet 44. Conductivity detector 42 may be of the same type as detector 20.

Means are provided for sparging the gases from the treated sample stream in the form of an overflow outlet 46 communicating with flow channel 36. Gases injected into the bottom of the reactor 22 rise to the top and overflow through line 46 to remove most of the gases from the system prior to detection by conductivity detector 42.

In operation, a liquid sample flows through flow control valve 14, pump 16 and flow meter 18 into the bottom of cylindrical housing 30. A suitable flow rate is on the order of 1 ml/min. to 10 ml/min. Simultaneously, oxygen flows through flow meter 28 at a typical rate of 10 ml/min. to 100 ml/min. and into the bottom of housing 30. At the bottom of the housing, the gas forms into a concentrated mass of bubbles which diffuse upwardly through the housing to provide oxygen bubbles dispersed in annular flow channel 36. The length of flow channel 36 is adjusted to provide adequate residence time for the organic compounds to be partially oxidized to their corresponding acid forms caused by irradiation with ultraviolet light emitted by lamp 34. The precise conditions to accomplish this objective are a function of the organic compounds in the sample, the flow of sample, the concentration of oxygen in the sample, the residence time, and the type of ultraviolet light emitted by the lamp. These parameters can be determined for the particular sample streams to be analyzed. The residence time may be controlled by adjusting the sample flow rate.

As discussed above, the conditions are maintained to assure that partial oxidation of the organic compounds in the sample rather than full oxidation are obtained. This is not difficult as complete oxidation of the organic compounds to carbon dioxide is slow and difficult with ultraviolet irradiation only. In that regard, it is preferable to exclude oxidation catalysts such as persulfate which are known to facilitate such complete conversion.

The major portion of the gas bubbles in the sample are permitted to overflow in the gas head space above the liquid level and out overflow pipe 46. The liquid outlet 40 is below the overflow pipe and so includes substantially all of the liquid flow in the system which passes through conductivity detector 42.

As set forth above, the conditions are adjusted to favor partial conversion to the acid form of the organic compounds rather than full conversion to carbon dioxide. However, at least a portion of the organic compounds typically will be fully oxidized. To more accurately measure the converted organic acids, it is preferable to remove entrained gases from the systems such as carbon dioxide and sulfur dioxide to avoid interference in the signal produced conductivity detector 42. However, it has been found that carbon dioxide does not produce a major increase in conductivity in comparison to organic acids. Accordingly, if desired, sparging of the gases may be eliminated.

In the illustrated embodiment, a conductivity detector 20 disposed prior to treatment of sample is used together with conductivity detector 42. Thus, detector 20 provides a constant background reading against which the signal of conductivity detector 42 is measured. An accurate detection of the organic compounds in the original stream which have been converted to ionizable acid form is accomplished by subtracting the background conductivity detected in detector 20 from the conductivity signal of detector 42. However, conductivity detector 20 is optional for those sample streams in which the background conductivity is relatively constant or where it is extremely low, such as process water in a semiconductor plant. However, if the source of sample is subject to wide variations in background conductivity, it would be preferable to include the additional conductivity detector.

It has been found that the oxidation intermediates (organic acids) are strongly ionized in comparison to the complete oxidation product of carbon dioxide. A relatively short residence time is required for such partial conversion. Thus, the sample stream itself containing such oxidation intermediates can be continously reacted in a reasonably sized reactor. This permits continuous flow through conductivity detector 42 for constant measurement without the requirement of periodic sample injection. Once the oxidation conditions are predetermined for the particular sample to be analyzed, the response is highly stable and reproducable.

It is noted that the photochemical oxidation of various organic compounds produce many different intermediates and the reaction kinetics are also different. Therefore, different compounds produce different conductivity signals. Some examples are shown below based on initial concentration of each organic compound of 50 ppm of carbon content in the sample:

|  | Response mmho |
| --- | --- |
| Acetone | 59.4 |
| Methanol | 20 |
| Propanol | 86.4 |
| Citric Acid | 120 |
| Acetic Acid | 61 |
| Sucrose | 120 |
| Phenol | 140 |

Photochemical oxidation of organics is relatively complicated. Accordingly, the same response will not be obtained from the oxidation of different organics. The system is very useful when there is little variation in the overall chemical compositions of the samples to be detected. The system is particularly effective in measuring a spill or sudden increase of the concentration of an organic compound into a nearly constant background sample stream.

In addition to the foregoing detection of organics, the system can also detect sudden increases in ionized inorganics to set off an alarm (not shown) if the conductivity exceeds the present level. For example, such inorganic compounds may include ionized salts, chlorine or acids which may spill into the system.

In order to more clearly illustrate the present invention, the following specific example of its practice is employed:

EXAMPLE

In this system, apparatus of the type schematically disclosed is utilized with the exception that conductivity detector 20 is not employed. The sample includes methanol in water at a concentration of 50 ppm of carbon at a constant flow rate of 1.5 ml/min. Oxygen at a flow rate of 15 ml/min. is fed into the bottom of the reactor. The UV light is emitted from a 30 watt lamp supplied by Jelight.

About 6% of the methanol is converted to formic acid to provide a conductance of 65 $\mu$mho. Conversely, about 45% of the methanol is converted to carbon dioxide which provided a conductance of only 5 $\mu$mho. The methanol and other intermediaries remaining (49%) do not affect conductance. In this example, it is apparent that over 90% of the total conductance is due to the formic acid even though only about 6% of methanol is converted to formic acid.

What is claimed:

1. A method of continuously monitoring an aqueous sample stream for organics by detecting at least one organic compound in said aqueous sample stream, said at least one organic compound being capable of being partially oxidized to an acid form, said method comprising,
   (a) continuously flowing an aqueous sample stream through a flow-through channel of an ultraviolet light reaction zone,
   (b) continuously irradiating said sample stream in said reaction zone with ultraviolet light in the presence of oxygen under conditions to partially oxidize, but not completely oxidize to carbon dioxide, at least some organic compound thereof for conversion to a corresponding ionized organic acid, not carbonic acid, and
   (c) continuously flowing said irradiated sample stream through a first conductivity detector in which the conductivity of the sample flowing therethrough is detected as an indication of the presence of organic compounds in the sample stream which have been converted to ionized organic acid, the major portion of said detected conductivity being produced by said ionized organic acid in comparison to carbonic acid.

2. The method of claim 1 in which, prior to step (a), background conductivity of said sample stream is detected by a second conductivity detector.

3. The method of claim 1 in which a source of oxygen gas is injected into said reaction zone.

4. The method of claim 3 in which gases are sparged from said sample stream prior to detection by said first conductivity detector.

* * * * *